United States Patent
Moeller et al.

(10) Patent No.: US 11,278,222 B2
(45) Date of Patent: Mar. 22, 2022

(54) WATERLESS ELECTROCHEMICAL TRANSDERMAL ALCOHOL SENSOR AND WEARABLE TRANSDERMAL ALCOHOL SENSOR DEVICE

(71) Applicant: Giner, Inc., Newton, MA (US)

(72) Inventors: Michael Moeller, Boston, MA (US); Brian Rasimick, Boston, MA (US)

(73) Assignee: 1A SMART START LLC, Grapevine, TX (US)

( * ) Notice: Subject to any disclaimer, the term of this patent is extended or adjusted under 35 U.S.C. 154(b) by 741 days.

(21) Appl. No.: 15/894,255

(22) Filed: Feb. 12, 2018

(65) Prior Publication Data

US 2019/0246958 A1 Aug. 15, 2019

(51) Int. Cl.
*A61B 5/1477* (2006.01)
*G01N 27/403* (2006.01)
(Continued)

(52) U.S. Cl.
CPC ........ *A61B 5/1477* (2013.01); *A61B 5/14546* (2013.01); *A61B 5/4845* (2013.01);
(Continued)

(58) Field of Classification Search
CPC ... A61B 5/4845; A61B 5/14546; A61B 5/681; G01N 27/407; G01N 27/4074; G01N 33/4972
See application file for complete search history.

(56) References Cited

U.S. PATENT DOCUMENTS

| 5,944,661 A | 8/1999 | Swette et al. |
| 6,792,793 B2 | 9/2004 | Mendoza |

(Continued)

FOREIGN PATENT DOCUMENTS

| JP | 2005118177 A | 5/2005 |
| JP | 2009229285 A | 10/2009 |

(Continued)

OTHER PUBLICATIONS

Martin et al., "Tonic and Phasic Processes in the Acute Effects of Alcohol," Experimental and Clinical Psychopharmacology, 14(2):209-218 (2006).

(Continued)

*Primary Examiner* — Puya Agahi
(74) *Attorney, Agent, or Firm* — Kriegsman & Kriegsman

(57) ABSTRACT

Waterless electrochemical transdermal alcohol sensor. In one embodiment, the sensor includes a proton exchange membrane imbibed with an imbibing liquid that includes at least one cationic substance that is liquid at room temperature. As examples, the cationic substance may be one or more ionic liquids with an imidazolium, phosphonium, ammonium, pyridinium, pyrrolidinium, or sulfonium backbone structure. The imbibing of the proton exchange membrane with the cationic substance obviates the need for the periodic addition of water to the electrochemical cell. The sensor additionally includes a sensing electrode, which is bonded to one side of the proton exchange membrane, and a counter electrode and a reference electrode, both of which are bonded to the opposite side of the proton exchange membrane. The sensor may be incorporated into a wearable transdermal alcohol sensor device, which, in turn, may be incorporated into a system for detecting transdermal alcohol.

24 Claims, 5 Drawing Sheets

(51) Int. Cl.
*G01N 27/40* (2006.01)
*A61B 5/00* (2006.01)
*A61B 5/145* (2006.01)
*G01N 27/407* (2006.01)
*G01N 33/497* (2006.01)

(52) U.S. Cl.
CPC ........... *G01N 27/40* (2013.01); *G01N 27/403* (2013.01); *A61B 5/681* (2013.01); *A61B 2560/0252* (2013.01); *A61B 2562/125* (2013.01); *G01N 27/407* (2013.01); *G01N 27/4074* (2013.01); *G01N 33/4972* (2013.01)

(56) References Cited

U.S. PATENT DOCUMENTS

| | | | |
|---|---|---|---|
| 7,087,150 | B2 | 8/2006 | Feng |
| 8,010,663 | B2 | 8/2011 | Firminger et al. |
| 8,165,824 | B2 | 4/2012 | Iiams et al. |
| 8,172,998 | B2 | 5/2012 | Bennett et al. |
| 9,548,501 | B2 | 1/2017 | Zhong et al. |
| 9,788,772 | B2 | 10/2017 | Nothacker et al. |
| 9,816,959 | B2 | 11/2017 | Umasankar et al. |
| 10,182,752 | B2 | 1/2019 | Nothacker et al. |
| 2004/0236199 | A1 | 11/2004 | Hawthorne et al. |
| 2009/0182216 | A1 | 7/2009 | Roushey, III et al. |
| 2010/0133120 | A1 | 6/2010 | Varney et al. |
| 2014/0210627 | A1 | 7/2014 | Nothacker et al. |
| 2014/0251834 | A1 | 9/2014 | Chen et al. |
| 2014/0365142 | A1 | 12/2014 | Baldwin |
| 2015/0164416 | A1 | 6/2015 | Nothacker et al. |
| 2016/0327542 | A1 | 11/2016 | Nothacker et al. |
| 2016/0338627 | A1 | 11/2016 | Lansdorp et al. |
| 2017/0086714 | A1 | 3/2017 | Nothacker et al. |
| 2017/0250412 | A1 | 8/2017 | Wei |
| 2017/0299542 | A1 | 10/2017 | Amouzadeh Tabrizi et al. |
| 2018/0209955 | A1 | 7/2018 | Moeller |

FOREIGN PATENT DOCUMENTS

| | | |
|---|---|---|
| WO | 2018136558 A1 | 7/2018 |
| WO | 2019156689 A1 | 8/2019 |

OTHER PUBLICATIONS

Piasecki et al., "Hangover and Risk for Alcohol Use Disorders: Existing Evidence and Potential Mechanisms," Curr Drug Abuse Rev., 3(2):92-102 (2010).

Piasecki et al., "Responses to Alcohol and Cigarette Use During Ecologically Assessed Drinking Episodes," Psychopharmacology, 223(3): 331-344 (2012).

Sakai et al., "Validity of Transdermal Alcohol Monitoring: Fixed and Self-Regulated Dosing," Alcoholism: Clinical and Experimental Research, 30(1):26-33 (2006).

Simons et al., "Quantifying alcohol consumption: Self-report, transdermal assessment, and prediction of dependence symptoms," Addictive Behaviors, 50:205-212 (2015).

Zhou et al., "Bi- and tri-metallic Pt-based anode catalysts for direct ethanol fuel cells," Journal of Power Sources, 131:217-223 (2004).

International Search Report dated May 14, 2018, in PCT Application No. PCT/US18/17838, the corresponding PCT application.

Written Opinion dated May 14, 2018, in PCT Application No. PCT/US18/17838, the corresponding PCT application.

Jones, "Quantitative measurements of the alcohol concentration and the temperature of breath during a prolonged exhalation," Acta Physiol Scand, 114:407-412 (1982).

WATERLESS ELECTROCHEMICAL TRANSDERMAL ALCOHOL SENSOR AND WEARABLE TRANSDERMAL ALCOHOL SENSOR DEVICE

FEDERALLY SPONSORED RESEARCH OR DEVELOPMENT

This invention was made with government support under R43 AA024649 awarded by National Institutes of Health. The government has certain rights in the invention.

BACKGROUND

The present invention relates generally to alcohol sensors and relates more particularly to electrochemical transdermal alcohol sensors.

Unlike breathalyzers, which use deep lung samples to measure alcohol present in a subject's breath, transdermal alcohol sensors measure alcohol vapor that diffuses through a subject's skin. The measured alcohol vapor diffusing through the skin is then correlated to a blood alcohol concentration (BAC). Transdermal alcohol sensors are able to monitor passively and continuously the alcohol vapor diffusing through the skin, and do not require periodic active participation from the subject, such as requiring that the subject provide a breath sample to a breathalyzer device.

Conventional transdermal alcohol sensors typically require the addition of water to the sensor due to the materials used in the sensor and the electrochemical measurement technique employed by the sensor. An example of a conventional transdermal alcohol sensor is disclosed in U.S. Pat. No. 5,944,661, inventors Swette et al., which issued Aug. 31, 1999, and which is incorporated herein by reference in its entirety (hereinafter "the '661 patent"). The '661 patent discloses a sensor comprising a three-electrode system (i.e., sensing electrode, counter electrode and reference electrode) and a proton exchange membrane (PEM). According to the '661 patent, the sensing electrode and the counter electrode are mechanically adhered to one side of the PEM, and the reference electrode is mechanically adhered to the opposing side of the PEM. The foregoing assembly is packaged in a sensor housing, and a water reservoir provides water to the reference electrode side of the PEM. As described in the '661 patent, the purpose of the water reservoir is to provide proton conductivity for the reactions taking place at the sensing and counter electrodes. This is because, in the absence of water and under low humidity conditions, the PEM loses ionic conductivity. Depending on PEM hydration levels, the loss of ionic conductivity in the PEM partially or fully inhibits the electrochemical oxidation of ethanol.

The lack of PEM hydration is particularly a problem for transdermal alcohol sensors of the type described in the '661 patent. This is at least for the reason that access holes need to be provided in the sensor housing so that alcohol vapor diffusing from the skin can diffuse to the sensing electrode located inside the sensor housing. However, these same access holes tend to allow water to diffuse out of the PEM—a problem that is exacerbated when the sensor is not being worn and is exposed to low ambient humidity conditions. Furthermore, as the sensor goes through one or more dehydration and rehydration cycles, the PEM tends to expand and to contract. Unfortunately, the expansion and contraction of the PEM tends to weaken the mechanical bond between the electrodes and the PEM and, thus, degrades the interface between the catalyst on the electrodes and the PEM. In turn, the degraded interface between the electrodes and the PEM inhibits the electrochemical oxidation of alcohol. This is because the electrochemical oxidation of alcohol takes place where alcohol vapor comes into contact with the interface between the electrodes and the PEM (i.e., the reaction triple-point).

In the field of high-temperature fuel cells, ionic liquids have been used in place of water. This is because water readily evaporates at high temperatures, thus drying out the PEM and inhibiting the ionic conductivity and electrode reactions of the fuel cell. Therefore, ionic liquids with high boiling points are often used in these high-temperature applications to maintain ionic conductivity in the absence of water.

For electrochemical sensing technology, however, ionic liquids can have drawbacks. For instance, many ionic liquids have poor ionic conductivity in the temperature range spanning from room temperature to body temperature, i.e., the temperature range at which a transdermal alcohol sensor will generally operate. Furthermore, platinum and platinum-based catalysts typically perform best for the electrochemical oxidation of ethanol whereas many ionic liquids have been shown to poison platinum-based catalysts. Indeed, the '661 patent discloses the use of platinum black for all three electrodes of the transdermal alcohol sensor described therein. The '661 patent also describes the sensing electrode as being polarized at 0.0V above a platinum-air reference electrode (or approximately 1.06 vs. a normal hydrogen electrode (NHE))—a potential at which many ionic liquids will oxidize at the sensing electrode (or be reduced at the counter or reference electrodes).

Further issues with using ionic liquids in an electrochemical transdermal alcohol sensor include the ionic liquid hydrolyzing in the presence of water (or water vapor from air), excessive swelling of the PEM, causing the electrodes to delaminate, the de-protonation of the ionic liquid, causing it to volatilize, the large size of some ionic liquids that prevent them from being imbibed into the PEM, and ionic liquids that solidify at room temperature or body temperature and, thus, will not act as an ion conductor in transdermal sensing applications.

SUMMARY OF INVENTION

It is an object of the present invention to provide a novel electrochemical transdermal alcohol sensor.

It is another object of the present invention to provide an electrochemical transdermal alcohol sensor that addresses at least some of the shortcomings associated with existing electrochemical transdermal alcohol sensors.

Therefore, according to one aspect of the invention, there is provided a waterless electrochemical transdermal alcohol sensor, the waterless electrochemical transdermal alcohol sensor comprising (a) a proton exchange membrane, wherein the proton exchange membrane is imbibed with an imbibing liquid, wherein the imbibing liquid comprises at least one cationic substance, the at least one cationic substance being liquid at room temperature; (b) a sensing electrode, wherein the sensing electrode is bonded to the proton exchange membrane; (c) a counter electrode, wherein the counter electrode is bonded to the proton exchange membrane; and (d) a reference electrode, wherein the reference electrode is bonded to the proton exchange membrane.

In another, more detailed feature of the invention, the proton exchange membrane may comprise a solid cation exchange membrane.

In another, more detailed feature of the invention, the solid cation exchange membrane may comprise a solid perfluorosulfonic acid membrane.

In another, more detailed feature of the invention, the solid perfluorosulfonic acid membrane may have an equivalent weight of approximately 700-1200 EW and may have a thickness of approximately 0.003-0.015 inch.

In another, more detailed feature of the invention, the at least one cationic substance may comprise at least one member selected from the group consisting of a cationic liquid with an imidazolium backbone structure, a cationic liquid with a phosphonium backbone structure, a cationic liquid with an ammonium backbone structure, a cationic liquid with a pyridinium backbone structure, a cationic liquid with a pyrrolidinium backbone structure, and a cationic liquid with a sulfonium backbone structure.

In another, more detailed feature of the invention, the cationic liquid with an imidazolium backbone structure may be at least one member selected from the group consisting of 1-Ethyl-3-methylimidazolium tetrafluoroborate ($C_6H_{11}BF_4N_2$), 1-Butyl-3-methylimidazolium tetrafluoroborate ($C_8H_{15}BF_4N_2$), 1-Butyl-3-methylimidazolium hexafluoroantimonate ($C_8H_{15}F_6N_2Sb$), 1-Butyl-3-methylimidazolium hexafluorophosphate ($C_8H_{15}F_6N_2P$), 1-Dodecyl-3-methylimidazolium iodide ($C_{16}H_{31}IN_2$), 1-Ethyl-2, 3-dimethylimidazolium trifluoromethane sulfonate ($C_8H_{13}F_3N_2O_3S$), 1-Ethyl-3-methylimidazolium thiocyanate ($C_7H_{11}N_3S$), 1-Ethyl-3-methylimidazolium trifluoromethane sulfonate ($C_7H_{11}F_3N_2O_3S$), 1-Butyl-3-methylimidazolium bis(trifluoromethyl sulfonyl)imide ($C_{10}H_{15}F_6N_3O_4S_2$), 1,2-Dimethyl-3-propylimidazolium bis(trifluoromethyl sulfonyl)imide ($C_{10}H_{15}F_6N_3O_4S_2$), 1,2-Dimethyl-3-propylimidazolium tris(trifluoromethyl sulfonyl) methide ($C_{12}H_{15}F_9N_2O_6S_3$), 1-Ethyl-3-methylimidazolium bis(pentafluoroethyl sulfonyl)imide ($C_{10}H_{11}N_3O_4S_2$), 1-Ethyl-3-methylimidazolium bis(trifluoromethyl sulfonyl)imide ($C_8H_{11}F_6N_3O_4S_2$), 1-Butyl-3-methylimidazolium methyl sulfate ($C_9H_{18}N_2O_4S$), 1-Ethyl-3-methylimidazolium ethyl sulfate ($C_8H_{16}N_2O_4S$), 1-Ethyl-3-methylimidazolium hydrogen sulfate ($C_6H_{12}N_2O_4S$), 1-Butyl-3-methylimidazolium thiocyanate ($C_9H_{15}N_3S$), and 1-Ethyl-3-methylimidazolium methanesulfonate ($C_7H_{14}N_2O_3S$).

In another, more detailed feature of the invention, the cationic liquid with a phosphonium backbone structure may be at least one member selected from the group consisting of Trihexyltetradecylphosphonium bis(2,4,4-trimethyl-8-pentyl)phosphinate ($C_{48}H_{102}O_2P_2$), Trihexyltetradecylphosphonium bis(trifluoromethylsulfonyl)amide ($C_{34}H_{68}F_6NO_4PS_2$), Trihexyltetradecylphosphonium decanoate ($C_{42}H_{87}O_2P$), Trihexyltetradecylphosphonium dicyanamide ($C_{34}H_{68}N_3P$), Trihexyltetradecylphosphonium hexafluorophosphate ($C_{32}H_{68}F_6P_2$), and Trihexyltetradecylphosphonium tetrafluoroborate ($C_{32}H_{68}BF_4P$), Tri-isobutylmethylphosphonium tosylate ($C_{20}H_{37}O_3PS$).

In another, more detailed feature of the invention, the cationic liquid with an ammonium backbone structure may be at least one member selected from the group consisting of Methyl-trioctylammonium bis(trifluoromethyl-sulfonyl) imide ($C_{27}H_{54}F_6N_2O_4S_2$), and tetrabutylammonium heptadecafluorooctanesulfonate ($C_{24}H_{36}F_{17}NO_3S$).

In another, more detailed feature of the invention, the cationic liquid with a pyridinium backbone structure may be at least one member selected from the group consisting of 1-Butyl-3-methylpyridinium bis(trifluoromethyl sulfonyl) imide ($C_{12}H_{16}F_6N_2O_4S_2$), and 3-Methyl-1-propylpyridinium bis(trifluoromethyl sulfonyl)-imide ($C_{11}H_{14}F_6N_2O_4S_2$).

In another, more detailed feature of the invention, the cationic liquid with a pyrrolidinium backbone structure may comprise 1-Butyl-1-methylpyrrolidinium bis(trifluoromethyl-sulfonyl)imide ($C_{11}H_{20}F_6N_2O_4S_2$).

In another, more detailed feature of the invention, the cationic liquid with a sulfonium backbone structure may comprise tri ethyl sulfonium bis(trifluoromethylsulfonyl) imide ($C_8H_{15}F_6NO_4S_2$).

In another, more detailed feature of the invention, the imbibing liquid may consist of the at least one cationic substance.

In another, more detailed feature of the invention, the imbibing liquid may comprise the at least one cationic substance and a solvent, and the at least one cationic substance may be dissolved in the solvent.

In another, more detailed feature of the invention, the solvent may be selected from the group consisting of water, at least one alcohol, and combinations thereof.

In another, more detailed feature of the invention, the concentration of the at least one cationic substance in the solvent may comprise at least 30% cationic substance by volume.

In another, more detailed feature of the invention, at least one of the sensing electrode, the counter electrode and the reference electrode may comprise a substrate and a platinum-based catalyst, and the platinum-based catalyst may be coupled to the substrate.

In another, more detailed feature of the invention, the substrate may comprise a porous mesh or sinter fabricated from at least one material selected from the group consisting of platinum, gold, titanium, niobium, palladium, and gold.

In another, more detailed feature of the invention, at least one of the sensing electrode, the counter electrode and the reference electrode may further comprise platinum particles, and the platinum particles may be interposed between the substrate and the platinum-based catalyst.

In another, more detailed feature of the invention, the platinum-based catalyst may comprise one of platinum-black, platinum on carbon, a bi-metallic alloy of platinum and a second metal on carbon, and a tri-metallic alloy of platinum and two other metals on carbon.

In another, more detailed feature of the invention, the platinum-based catalyst may comprise platinum on carbon, and the weight percentage of platinum in the platinum on carbon may be approximately 10-70%, with the remainder being carbon.

In another, more detailed feature of the invention, the platinum-based catalyst may comprise the bi-metallic alloy of platinum and a second metal on carbon, the second metal may be selected from the group consisting of tin, ruthenium, palladium, nickel, cobalt, and tungsten, the weight percentage of platinum in the bi-metallic alloy may be approximately 20-70%, with the remainder being the second metal, and the weight of the bi-metallic alloy may be approximately 10-70%, with the remainder being carbon.

In another, more detailed feature of the invention, the platinum-based catalyst may comprise the tri-metallic alloy of platinum and two other metals on carbon, the two other metals may be two different metals selected from the group consisting of tin, ruthenium, palladium, nickel, cobalt, and tungsten, the weight percentage of platinum in the tri-metallic alloy may be approximately 10-70%, with the remainder being the two other metals in approximately a 1:1 ratio, by weight, with each other, and the weight of the tri-metallic alloy may be approximately 10-70%, with the remainder being carbon.

In another, more detailed feature of the invention, the platinum-based catalyst may further comprise an ionomer.

In another, more detailed feature of the invention, the ionomer may comprise perfluorosulfonic acid having an equivalent weight of approximately 700-1100 EW, and the ionomer may be present in the platinum-based catalyst in an amount constituting about 10-60% by weight.

In another, more detailed feature of the invention, the proton exchange membrane may have two opposing surfaces, the sensing electrode may be bonded to one of the two opposing surfaces, and both the counter electrode and the reference electrode may be bonded to the other of the two opposing surfaces.

According to another aspect of the invention, there is provided one embodiment of a method of making the above-described waterless electrochemical transdermal alcohol sensor, the method comprising the steps of (a) providing a proton exchange membrane, a sensing electrode, a counter electrode, and a reference electrode; (b) bonding each of the sensing electrode, the counter electrode, and the reference electrode to the proton exchange membrane under conditions of elevated pressure and elevated temperature for a period of time; and (c) then, imbibing the proton exchange membrane with an imbibing liquid, wherein the imbibing liquid comprises at least one cationic substance, the at least one cationic substance being liquid at room temperature.

In another, more detailed feature of the invention, the elevated pressure may comprise a pressure of at least 100 psi, the elevated temperature may be approximately 200-400° F., and the period of time may be approximately 1 second to 1 hour.

According to yet another aspect of the invention, there is provided another embodiment of a method of making the above-described waterless electrochemical transdermal alcohol sensor, the method comprising the steps of (a) providing a proton exchange membrane, a sensing electrode, a counter electrode, and a reference electrode; (b) imbibing the proton exchange member with an imbibing liquid, wherein the imbibing liquid comprises at least one cationic substance, the at least one cationic substance being liquid at room temperature; and (c) then, bonding each of the sensing electrode, the counter electrode, and the reference electrode to the imbibed proton exchange membrane under conditions of elevated pressure and elevated temperature for a period of time.

In another, more detailed feature of the invention, the imbibing step may comprise imbibing the proton exchange member with the imbibing liquid for a period of time in the range of approximately 10 seconds to 24 hours.

In another, more detailed feature of the invention, the elevated pressure may comprise a pressure of at least 100 psi, the elevated temperature may be approximately 10 degrees lower than the boiling point of the imbibing liquid or 400° F., whichever is lower, and the period of time may be approximately 1 second to 1 hour.

According to a further aspect of the invention, there is provided a wearable transdermal alcohol sensor device, the wearable transdermal alcohol sensor device comprising (a) a housing, the housing comprising an interior chamber and a first access opening to permit fluid access to the interior chamber; (b) the waterless electrochemical transdermal alcohol sensor as described above, the waterless electrochemical transdermal alcohol sensor being disposed within the interior chamber of the housing; (c) a power supply, the power supply being operatively coupled to the waterless electrochemical transdermal alcohol sensor; (d) electronics operatively coupled to the waterless electrochemical transdermal alcohol sensor for correlating signals generated by the waterless electrochemical transdermal alcohol sensor with blood alcohol measurements; and (e) means for coupling the housing to a user.

In another, more detailed feature of the invention, the wearable transdermal alcohol sensor device may further comprise a first gas permeable/liquid impermeable membrane, and the first gas permeable/liquid impermeable membrane may seal the first access opening and may be in fluid communication with the waterless electrochemical transdermal alcohol sensor.

In another, more detailed feature of the invention, the housing may further comprise a second access opening to permit fluid access to the interior chamber, the wearable transdermal alcohol sensor device may further comprise a combination temperature and humidity sensor and a second gas permeable/liquid impermeable membrane, the combination temperature and humidity sensor may be disposed within the housing, and the second gas permeable/liquid impermeable membrane may seal the second access opening and may be in fluid communication with the combination temperature and humidity sensor.

According to still a further aspect of the invention, there is provided a system for detecting transdermal alcohol, the system comprising (a) the wearable transdermal alcohol sensor device as described above; and (b) a user interface device in communication with the wearable transdermal alcohol sensor device.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numeral represent like parts:

FIG. 1b is a bottom view of the waterless transdermal alcohol sensor shown in FIG. 1a;

FIG. 2 is a schematic section view of the waterless transdermal alcohol sensor shown in FIG. 1a;

DETAILED DESCRIPTION OF INVENTION

The present invention is directed, in part, at a waterless transdermal alcohol sensor. For the purposes of this patent, "waterless" is defined as operation of the electrochemical transdermal alcohol sensor described herein without periodic additions of water to the electrochemical sensing system.

Figure 1A:
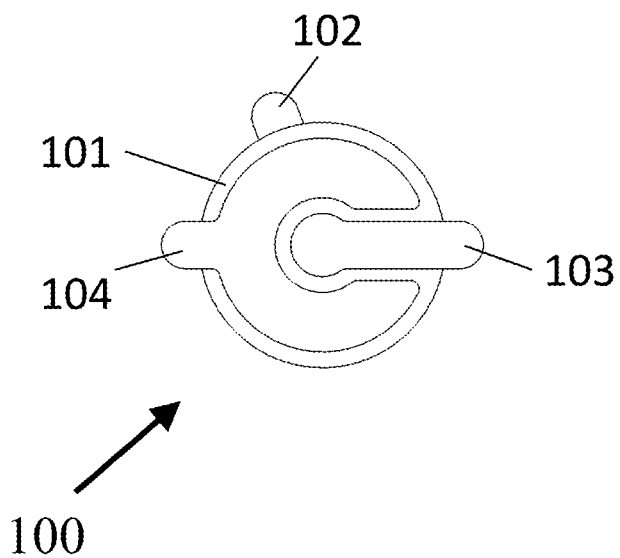
FIG. 1a is a top view of one embodiment of a waterless transdermal alcohol sensor constructed according to the teachings of the present invention.
Figure 1B:
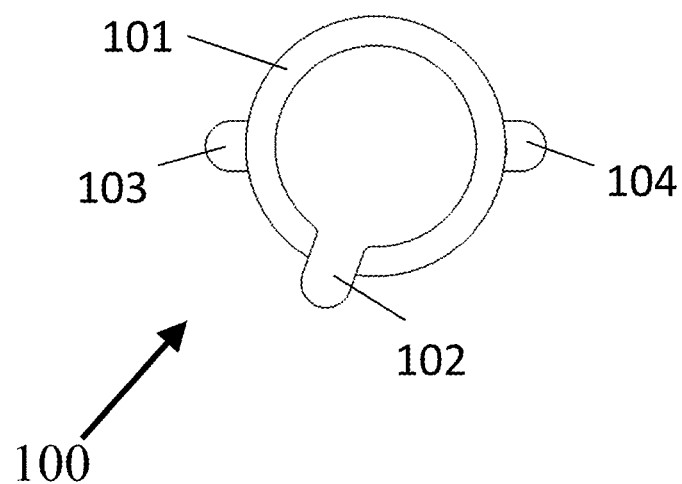
Figure 2:
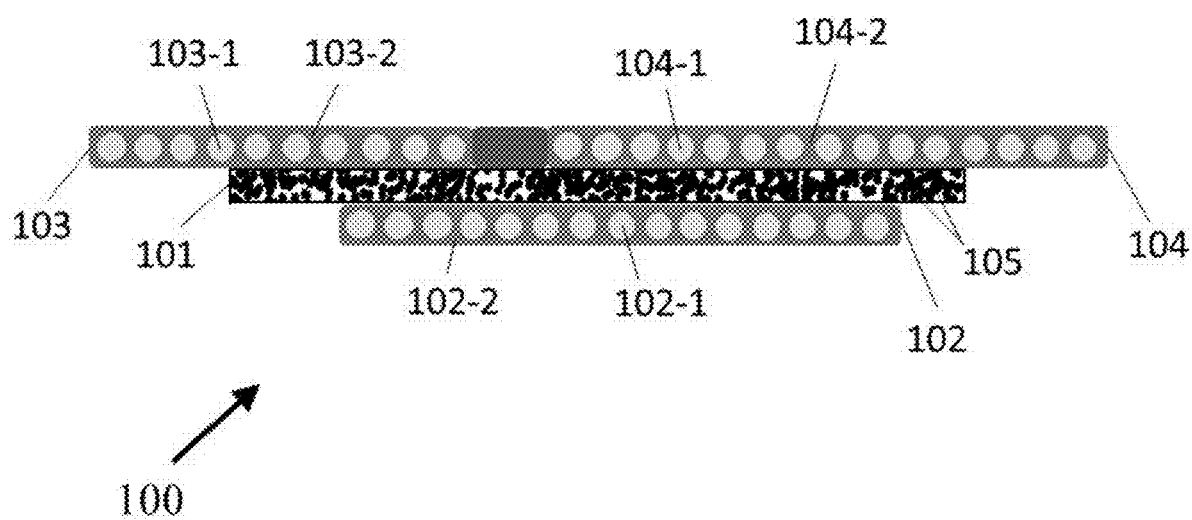

Referring to FIGS. 1a, 1b, and 2, there are shown various views of one embodiment of a waterless transdermal alcohol sensor constructed according to the present invention, the waterless transdermal alcohol sensor being represented generally by reference numeral 100.

Waterless transdermal alcohol sensor 100 may comprise a proton exchange membrane (PEM) 101, a sensing electrode 102, a reference electrode 103, and a counter electrode 104.

Proton exchange membrane 101, in turn, may comprise a solid cation exchange membrane. For example, the solid cation exchange membrane may be a solid perfluorosulfonic acid (PFSA) membrane. The PFSA membrane may have a preferred range of equivalent weights of approximately 700-1200 EW and may have a preferred thickness of approximately 0.003-0.015 inch. Examples of materials suitable for use as the PFSA membrane may include Nafion® 115, Nafion® 117, and Nafion® 1110 PFSA membranes.

Each of sensing electrode 102, reference electrode 103, and counter electrode 104 may comprise a substrate 102-1, 103-1, and 104-1 and a platinum-based catalyst 102-2, 103-2 and 104-2, the platinum-based catalysts 102-2, 103-2 and 104-2 being adhered to their respective substrates 102-1, 103-1 and 104-1. The substrates 102-1, 103-1 and 104-1 may each comprise a porous mesh or sinter fabricated from a material like platinum, gold, titanium, niobium, palladium, or tantalum. The aforementioned substrates 102-1, 103-1 and 104-1 may be further electro-plated with platinum particles, wherein the platinum particles may substantially cover the surface of the substrate material. The substrates 102-1, 103-1 and 104-1 may be coated with their respective platinum-based catalysts 102-2, 103-2 and 104-2, for example, by spraying a platinum-based catalyst ink onto the substrate, dry-pressing the platinum-based catalyst onto the substrate, roll-coating a platinum-based catalyst ink onto the substrate, or an equivalent means of coating a substrate with a catalyst.

The platinum-based catalysts 102-2, 103-2 and 104-2 may comprise platinum-black. Alternatively, the platinum-based catalysts 102-2, 103-2 and 104-2 may comprise platinum on carbon (Pt/C), wherein the weight percentage of platinum in the Pt/C catalyst composite is in the range of approximately 10-70%, with the remainder comprising carbon. In another alternative, the platinum-based catalysts 102-2, 103-2 and 104-2 may comprise a bi-metallic alloy of platinum and a second metal on carbon (Pt—X/C), wherein X may comprise a second metal, such as tin, ruthenium, palladium, nickel, cobalt, or tungsten. The weight percentage of platinum in the bi-metallic alloy may be in the range of approximately 20-70%, with the remainder comprising the second metal. The weight percentage of the bi-metallic alloy in the Pt—X/C mixture may be in the range of approximately 10-70%, with the remainder comprising carbon. In yet another alternative, the platinum-based catalysts 102-2, 103-2 and 104-2 may comprise a tri-metallic alloy of platinum and two other metals on carbon (Pt—X—Y/C), wherein X and Y may comprise two different metals selected from a group, such as tin, ruthenium, palladium, nickel, cobalt, and tungsten. The weight percentage of platinum in the tri-metallic alloy may be in the range of approximately 10-70%, with the remainder comprising the two other metals alloyed with platinum. The two other metals are preferably in approximately a 1:1 ratio, by weight, with each other. The weight percentage of the tri-metallic alloy in the Pt—X—Y/C mixture may be in the range of approximately 10-70%, with the remainder comprising carbon.

The platinum-based catalysts 102-2, 103-2 and 104-2 may further comprise an ionomer. The ionomer may comprise perfluorosulfonic acid (PFSA). A preferred range of equivalent weights for the ionomer may be approximately 700-1100 EW. An example of an ionomer that may be added to the platinum-based catalyst mixture is Nafion® 1100 equivalent weight. The ionomer may be present in the catalyst mixture in an amount in the range of approximately 10-60% by weight. The area of each electrode may comprise an area of at least 0.100 $mm^2$. The area of the counter electrode may comprise an area greater than or equal to the area of the sensing electrode.

Each of sensing electrode 102, reference electrode 103, and counter electrode 104 may be bonded to proton exchange membrane 101 by being mechanically pressed together with proton exchange membrane 101 at an appropriate pressure and at an appropriate temperature for an appropriate period of time. For example, the pressure at which each of sensing electrode 102, reference electrode 103, and counter electrode 104 may be pressed together with proton exchange membrane 101 may be a pressure of at least 100 psi. The temperature at which each of sensing electrode 102, reference electrode 103, and counter electrode 104 may be pressed together with proton exchange membrane 101 may be a temperature in the range of approximately 200-400 degrees Fahrenheit. The period of time for which each of sensing electrode 102, reference electrode 103, and counter electrode 104 may be pressed together with proton exchange membrane 101 may be in the range of approximately 1 second to 1 hour. Two or more of sensing electrode 102, reference electrode 103, and counter electrode 104 may be bonded to proton exchange membrane 101 simultaneously.

As shown in the present embodiment, sensing electrode 102 may be bonded to one side of proton exchange membrane 101, and each of reference electrode 103 and counter electrode 104 may be bonded to the opposite side of proton exchange membrane 101; however, other arrangements of sensing electrode 102, reference electrode 103 and counter electrode 104 on proton exchange membrane 104 are possible, such as, for example, bonding all three of sensing electrode 102, reference electrode 103 and counter electrode 104 to the same side of proton exchange membrane 101. Regardless of the particular arrangement employed, the combination of proton exchange membrane 101, sensing electrode 102, reference electrode 103, and counter electrode 104 may be referred to herein as a membrane electrode assembly (MEA).

As seen best in FIG. 2, waterless transdermal alcohol sensor 100 may further comprise an ionic liquid 105 imbibed into proton exchange membrane 101 of the MEA. (Although ionic liquid 105 is schematically shown in FIG. 2 as non-uniformly distributed throughout proton exchange membrane 101, it is to be understood that ionic liquid 105 is preferably distributed substantially uniformly throughout proton exchange membrane 101.)

Ionic liquid 105 may comprise a cation ionic liquid that is a liquid at room temperature. In particular, the cation ionic liquid may comprise an ionic liquid with an imidazolium, phosphonium, ammonium, pyridinium, pyrrolidinium, or sulfonium backbone structure.

Examples of an ionic liquid with an imidazolium backbone structure may include, but are not limited to, 1-Ethyl-3-methylimidazolium tetrafluoroborate ($C_6H_{11}BF_4N_2$), 1-Butyl-3-methylimidazolium tetrafluoroborate ($C_8H_{15}BF_4N_2$), 1-Butyl-3-methylimidazolium hexafluoroantimonate ($C_8H_{15}F_6N_2Sb$), 1-Butyl-3-methylimidazolium hexafluorophosphate ($C_8H_{15}F_6N_2P$), 1-Dodecyl-3-methylimidazolium iodide ($C_{16}H_{31}IN_2$), 1-Ethyl-2,3-dimethylimidazolium trifluoromethane sulfonate ($C_8H_{13}F_3N_2O_3S$), 1-Ethyl-3-methylimidazolium thiocyanate ($C_7H_{11}N_3S$), 1-Ethyl-3-methylimidazolium trifluoromethane sulfonate ($C_7H_{11}F_3N_2O_3S$), 1-Butyl-3-methylimidazolium bis(trifluoromethylsulfonyl)imide ($C_{10}H_{15}F_6N_3O_4S_2$), 1,2-Dimethyl-3-propylimidazolium bis(trifluoromethyl sulfonyl)imide ($C_{10}H_{15}F_6N_3O_4S_2$), 1,2-Dimethyl-3-propylimidazolium tris (trifluoromethyl sulfonyl)methide ($C_{12}H_{15}F_9N_2O_6S_3$), 1-Ethyl-3-methylimidazolium bis(pentafluoroethyl sulfonyl)imide ($C_{10}H_{11}N_3O_4S_2$), 1-Ethyl-3-methylimidazolium bis(trifluoromethyl sulfonyl)imide ($C_8H_{11}F_6N_3O_4S_2$), 1-Butyl-3-methylimidazolium methyl sulfate ($C_9H_{18}N_2O_4S$), 1-Ethyl-3-methylimidazolium ethyl sulfate ($C_8H_{16}N_2O_4S$), 1-Ethyl-3-methylimidazolium hydrogen sulfate ($C_6H_{12}N_2O_4S$), 1-Butyl-3-methylimidazolium thiocyanate ($C_9H_{15}N_3S$), and 1-Ethyl-3-methylimidazolium methanesulfonate ($C_7H_{14}N_2O_3S$).

Examples of an ionic liquid with a phosphonium backbone structure may include, but are not limited to, Trihexyltetradecylphosphonium bis(2,4,4-trimethyl-8-pentyl) phosphinate ($C_{48}H_{102}O_2P_2$), Trihexyltetradecylphosphonium bis(trifluoromethylsulfonyl)amide ($C_{34}H_{68}F_6NO_4PS_2$), Trihexyltetradecylphosphonium decanoate ($C_{42}H_{87}O_2P$), Trihexyltetradecylphosphonium dicyanamide ($C_{34}H_{68}N_3P$), Trihexyltetradecylphosphonium hexafluorophosphate ($C_{32}H_{68}F_6P_2$), and Trihexyltetradecylphosphonium tetrafluoroborate ($C_{32}H_{68}BF_4P$), Triisobutylmethylphosphonium tosylate ($C_{20}H_{37}O_3PS$).

Examples of an ionic liquid with an ammonium backbone structure may include, but are not limited to, Methyltrioctylammonium bis(trifluoromethyl-sulfonyl)imide ($C_{27}H_{54}F_6N_2O_4S_2$), and tetrabutylammonium heptadecafluorooctanesulfonate ($C_{24}H_{36}F_{17}NO_3S$).

Examples of an ionic liquid with a pyridinium backbone structure may include, but are not limited to, 1-Butyl-3-methylpyridinium bis(trifluoromethylsulfonyl)imide ($C_{12}H_{16}F_6N_2O_4S_2$), and 3-Methyl-1-propylpyridinium bis(trifluoromethylsulfonyl)-imide ($C_{11}H_{14}F_6N_2O_4S_2$).

An example of an ionic liquid with a pyrrolidinium backbone structure may include, but is not limited to, 1-Butyl-1-methylpyrrolidinium bis(trifluoromethyl-sulfonyl)imide ($C_{11}H_{20}F_6N_2O_4S_2$).

An example of an ionic liquid with a sulfonium backbone structure may include, but is not limited to, triethylsulfonium bis(trifluoromethylsulfonyl)imide ($C_8H_{15}F_6NO_4S_2$).

The ionic liquid may be dissolved in a suitable solvent prior to being imbibed, with the ionic liquid solution thereafter being imbibed into the proton exchange membrane. The solvent for the ionic liquid solution may comprise water, an alcohol (e.g., ethanol, methanol, propylene glycol, polyethylene glycol, or the like), or a combination of water and an alcohol. The concentration of the ionic liquid in the solvent may comprise at least 30% ionic liquid by volume. The proton exchange membrane may be imbibed with the ionic liquid or ionic liquid solution, for example, by soaking the MEA in the ionic liquid or ionic liquid solution for an appropriate period of time, for example, approximately 10 seconds to 24 hours. After soaking in the ionic liquid or ionic liquid solution, any excess ionic liquid or ionic liquid solution on the surface of the MEA may be wiped off.

In an alternative embodiment, proton exchange membrane 101 may be soaked in the ionic liquid (or ionic liquid solution) prior to bonding sensing electrode 102, reference electrode 103 and counter electrode 104 to proton exchange membrane 101. The ionic liquid (or ionic liquid solution) that is imbibed into the proton exchange membrane may comprise the same or substantially similar ionic liquid (or ionic liquid solution) as described above. After soaking the proton exchange membrane in the ionic liquid (or ionic liquid solution), the sensing, reference, and counter electrodes may be bonded to the proton exchange membrane by pressing the respective electrode together with the imbibed proton exchange membrane at a specified pressure, temperature, and time. The pressure at which the electrodes and the proton exchange membrane are pressed together may be a pressure of at least 100 psi. The temperature at which the electrodes and the proton exchange membrane may be pressed together may be at least 10 degrees lower than the boiling point of the ionic liquid (or ionic liquid solution). Alternatively, the proton exchange membrane and the electrodes may be pressed together at a temperature in the range of approximately 250-400 degrees Fahrenheit. The period of time during which the electrodes and the proton exchange membrane are pressed together at the aforementioned temperature and pressure may be a time in the range of approximately 1 second to 1 hour. Two or more of the sensing, reference, and counter electrodes may be simultaneously bonded to the proton exchange membrane.

The present invention is also directed at a system for detecting transdermal alcohol using waterless trans dermal alcohol sensor 100.

Figure 3:
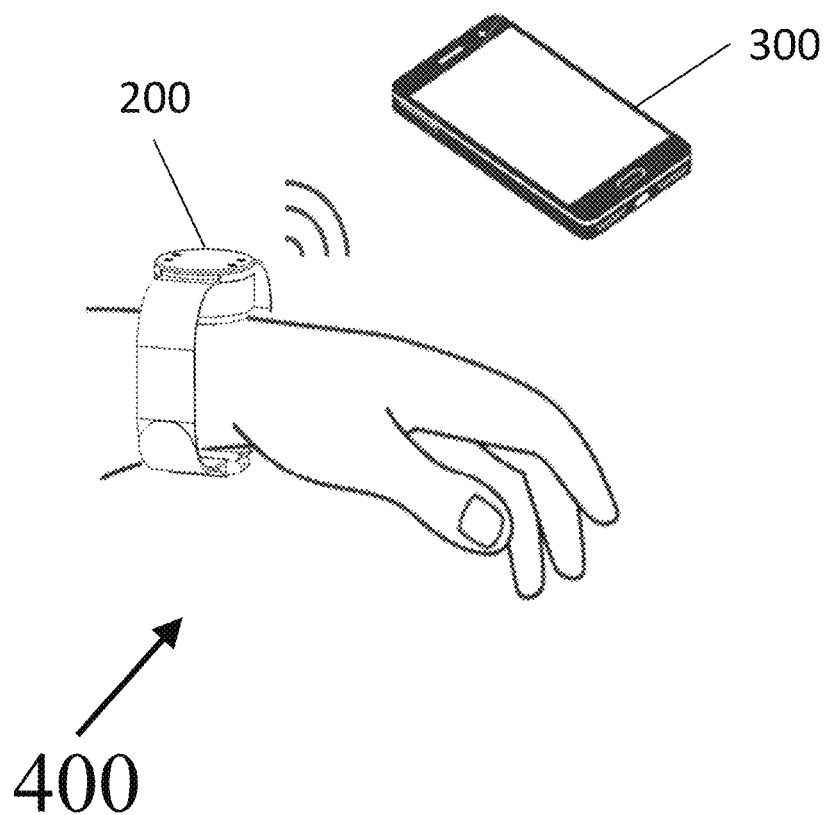
FIG. 3 is a perspective view of one embodiment of a system for transdermal alcohol detection, the system being constructed according to the teachings of the present invention and including a wearable transdermal alcohol sensor device, which is shown worn on the wrist of a person.

Referring to FIG. 3, there is shown one embodiment of a system for detecting transdermal alcohol, the system being constructed according to the present invention and being represented generally by reference numeral 400.

System 400 may comprise a transdermal alcohol sensor device 200 and a user interface device 300, wherein transdermal alcohol sensor device 200 and user interface device 300 are capable of communicating with each other. User interface device 300 may comprise a smartphone, tablet, PC, or similar device. User interface device 300 may further comprise a software application to process the device signals for the detection of transdermal alcohol and to enable verification of user identity.

Transdermal alcohol sensor device 200 may be worn around the wrist of a user so that alcohol vapor diffusing through the skin of the user may diffuse to an alcohol sensing component contained inside transdermal alcohol sensor device 200. Alternatively, transdermal alcohol sensor device 200 may be secured at other locations on a user's body that provide transdermal alcohol sensor device 200 with access to the alcohol vapor diffusing through the skin of the user, such as around the ankle. Both transdermal alcohol sensor device 200 and user interface device 300 possess the capability to transmit and receive information using Bluetooth, Bluetooth Low Energy, cellular, or an equivalent wireless means of communication.

Figure 4:
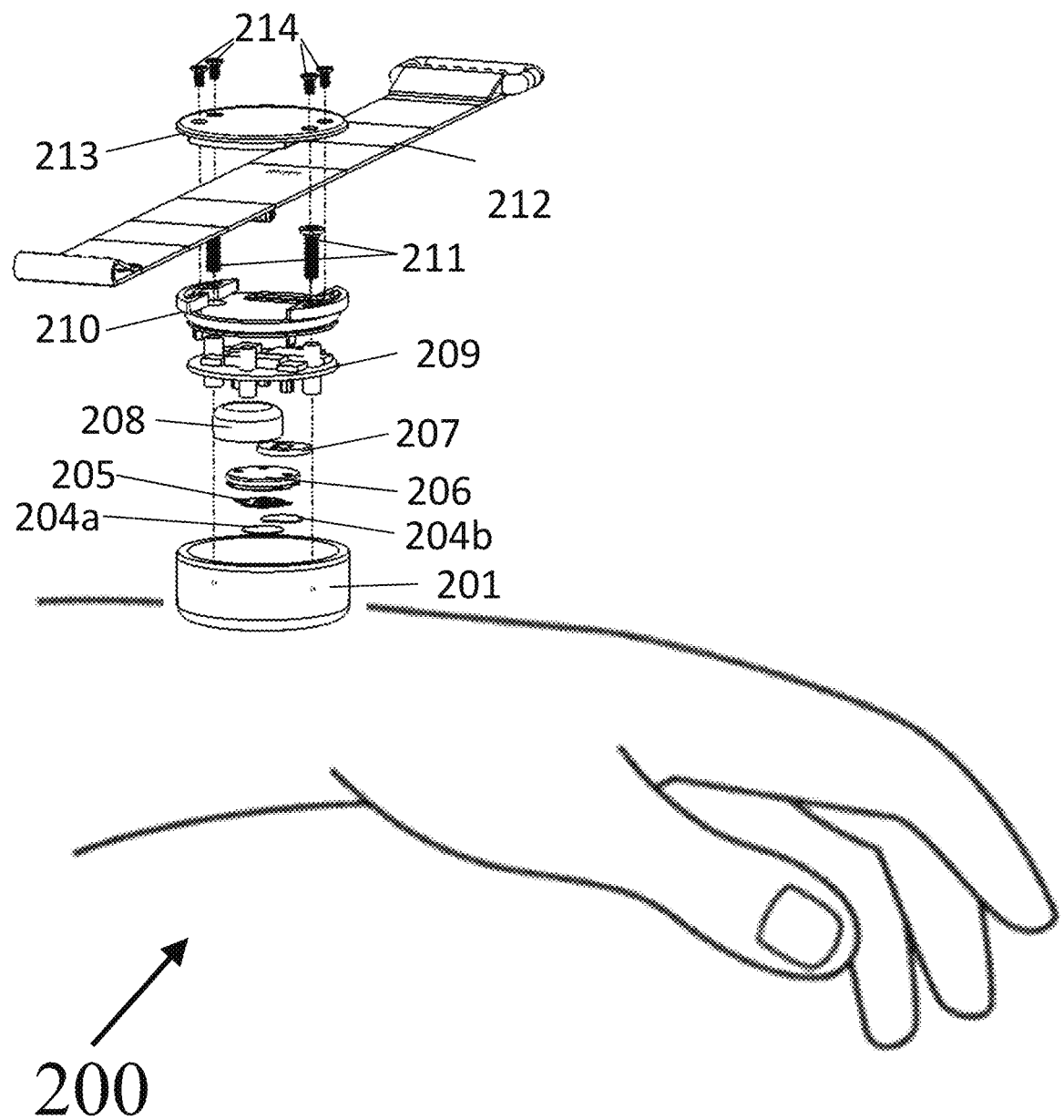
FIG. 4 is an enlarged exploded perspective view of the wearable transdermal alcohol sensor device shown in FIG. 3.
Figure 5:
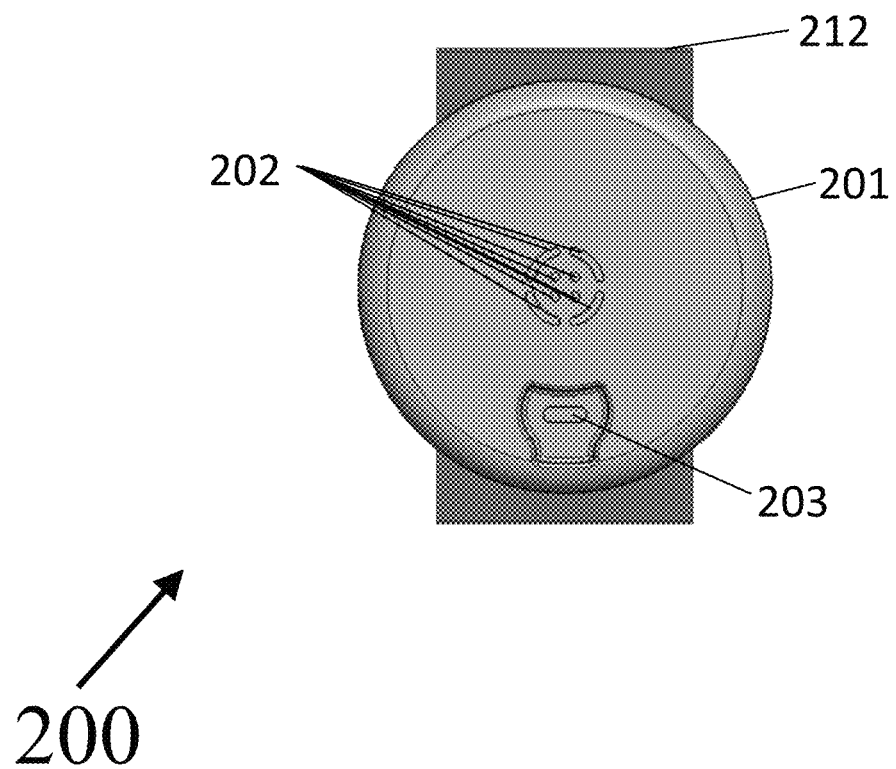
FIG. 5 is a fragmentary bottom view of the wearable transdermal alcohol sensor device shown in FIG. 4.

Referring now to FIG. 4, an exploded perspective view of transdermal alcohol sensor device 200 is shown. Device 200 may comprise a bottom housing 201 that may be placed in direct physical contact with the skin of a user. Bottom housing 201 may be provided with one or more access slots 202 on a bottom wall (see FIG. 5) that allow alcohol vapor diffusing through the skin of a user to also diffuse into the interior of bottom housing 201. Bottom housing 201 also may be provided with at least one access slot 203 on a bottom wall (see FIG. 5) that allows vapor diffusing from the skin or from ambient air to diffuse into the interior of bottom housing 201.

Device 200 may further comprise gas permeable/liquid impermeable membranes 204a and 204b. Gas permeable/liquid impermeable membranes 204a and 204b may seal access slots 202 and 203, respectively, on the interior of bottom housing 201. Each of gas permeable/liquid impermeable membranes 204a and 204b may be sealed against the top surface of the bottom wall of bottom housing 201 using ultrasonic welding, heat-bonding, gasketing, or an equivalent means. Gas permeable/liquid impermeable membranes 204a and 204b comprise membranes that are permeable to vapor (e.g. alcohol vapor, air), but impermeable to liquids. Examples of materials that may be used as each of gas permeable/liquid impermeable membranes 204a and 204b may include, but are not limited to, a silicone membrane, a silicone polycarbonate composite membrane, a liquid impermeable polytetrafluoroethylene (PTFE) membrane, a liquid impermeable polyvinylidene fluoride (PVDF) membrane, or any equivalent gas permeable/liquid impermeable membranes.

As alcohol vapor diffuses through gas permeable/liquid impermeable membrane 204a, the alcohol vapor may then be oxidized by an alcohol sensor 205. Alcohol sensor 205 may consist of or comprise the same or a substantially similar alcohol sensor as waterless transdermal alcohol sensor 100. Analogously, vapor from the skin or from ambient air may diffuse through gas permeable/liquid impermeable membrane 204b, wherein temperature and humidity may be detected by a combination temperature and humidity sensor 207. An example of a combination temperature and humidity sensor may be Texas Instruments® HDC1080DMBT temperature/humidity sensor. The combination temperature and humidity sensor 207 may be electrically-coupled or electrically-connected to an electronics board 209. Alternatively, separate temperature and humidity sensors may be electrically-coupled or electrically-connected to electronics board 209.

Device 200 may further comprise a sealing cap 206 to provide a sealed enclosure for alcohol sensor 205. Sealing cap 206 may further provide electrical connections (not shown) to the sensing, counter, and reference electrodes of alcohol sensor 205 using gold pins sealed or molded within sealing cap 206, wherein the bottom of each gold pin may be electrically-connected to one of the electrodes of alcohol sensor 205 and the top of each gold pin may be accessed on a top side of sealing cap 206.

As alluded to above, device 200 may further comprise an electronics board 209, which, in turn, may comprise electrical contacts (not shown), such as gold pins, that are in electrical connection with each of the gold pins on the surface of sealing cap 206. Electronics board 209 may further comprise the same or a substantially similar potentiostatic control circuit, as is used in the '661 patent, using said electrical connections to sensing, counter, and reference electrodes. Electronics board 209 may further comprise a proximity sensor (not shown), preferably a capacitive proximity sensor, that is able to detect proximity to human skin. An example of such a capacitive sensor is the Cypress Semiconductor CapSense® series sensor (CY8CMBR3xxx). In the case of a capacitive proximity sensor, the proximity sensor may be electrically-connected to a sensor pad (not shown), wherein the sensor pad preferably comprises copper with a non-conductive film overlay. The sensor pad may be a trace (not shown) on electronics board 209 that is any shape, but preferably the shape of a ring. The sensor pad preferably has an area of at least 2.0 $mm^2$.

Electronics board 209 may further comprise a microprocessor (not shown) for supplying power to the potentiostatic circuit, the temperature/humidity sensor, and the proximity sensor. The microprocessor preferably also reads the analog or digital signals from the potentiostatic circuit, the temperature/humidity sensor, and the proximity sensor at separate A/D or I/O channels. Each of the analog or digital signals may be read and stored up to every 1 second. Preferably, the signals may be read every approximately 1-30 seconds and averaged over an approximately 1-10 minute interval. Unlike transdermal alcohol sensor devices using Breathalyzer fuel cells that need a sample pumped to the fuel cell, the present invention uses the passive diffusion of alcohol vapor to the device, and the three-electrode sensor design continuously oxidizes the alcohol vapor that reaches the sensing electrode. That is, the present invention does not measure discrete samples like a transdermal alcohol sensor device using a fuel cell; rather, the signal generated from the transdermal alcohol sensor of the present invention is continuously available from the potentionstatic circuit at the dedicated A/D channel on the microprocessor. The analog or digital signals collected and stored on the electronics board may be converted to engineering units wherein the engineering units are degrees Celsius or Fahrenheit for the temperature, % relative humidity for the humidity sensor, pico-Farads for the proximity sensor, and mg/dL or % BAC for the alcohol sensor. The raw signals (i.e., the raw count values) read into the A/D or I/O channels may be converted by the firmware to the aforementioned engineering units using supplied calibration curves from the manufacturer. In the case of the alcohol sensor, the calibration curve is established by measuring the analog signal (i.e., the current out of the potentiostatic circuit that is converted to voltage) over one or more known concentrations of alcohol corresponding to relevant blood alcohol concentrations (i.e., measuring the vapor phase alcohol over an alcohol known alcohol bath at body temperature in the range of human % BAC concentrations).

Electronics board 209 may further comprise a wireless communication module (not shown) so that information may be transmitted to and received from user interface device 300. Examples of such a wireless communication module may comprise, but are not limited to, Texas Instruments™ CC2540 chip for Bluetooth low energy data transmission and Ublox Sara G-3 series chip for cellular transmission. The raw signals, averaged raw signals, raw signals converted to engineering units, or averaged raw signals converted to engineering units may be transmitted up to every 1 second by the wireless communication module. Alternatively, the signals may be transmitted by the wireless communication module to the user interface device every approximately 1 minute to 24 hours, preferably every approximately 10-30 minutes.

Device 200 may further comprise a battery 208 for supplying power to alcohol sensing element 205 and/or electronics board 209. Battery 208 may comprise a rechargeable or non-rechargeable coin cell battery.

Device 200 may further comprise a top housing 210, which may be secured against bottom housing 201 using one or more screws 211 to provide a sealed enclosure for battery 208, alcohol sensing element 205, temperature/humidity sensor 207, electronics board 209, and the other internal components of device 200.

Device 200 may further comprise a wristband 212, which may be secured between top housing 210 and a strap retainer 213 using one or more screws 214. Instead of using a wristband to couple device 200 to a person, device 200 may use structures like a bracelet, a necklace, or a ring or may use fastening implements, such as bio-compatible adhesives or the like.

System 400 may further comprise a software application on user interface device 300. The software application preferably receives and graphs the raw signals transmitted by the wireless communication module of device 200. The software application may convert the raw signals to engineering units using the same conversion technique as is potentially implemented by the firmware (described above). Alternatively, the software application may receive and graph the raw signals converted to engineering units. The software application may provide an alert when a drinking event has been detected. For the purposes of this invention, a drinking event is defined as a net response by the alcohol sensor of 10 mg/dL (0.010% BAC) or greater over the background sensor signal. The software application may also provide an alert of user non-compliance wherein user non-compliance is determined by one or more of the temperature, humidity, and proximity sensor signals. The software application may provide a user non-compliance alert when the temperature sensor measures a temperature that is outside the range of skin temperature, when the humidity sensor measures a % RH that is outside the range of % RH provided by the human body (generally >95% RH), or the proximity sensor measures a signal that is not consistent with the proximity to human skin. The software application may further comprise pinging device 200 on-demand wherein the on-demand ping causes device 200 to send the signals within 5 minutes of the ping.

In an alternative embodiment, device 200 may only transmit the raw signals or the raw signals converted to engineering units to the user interface device when a change in one or more of the signals has been detected. The change in the alcohol signal that would cause a transmission of one or more of the signals may comprise a change in the alcohol signal of 10 mg/dL (or the corresponding raw count value) or greater. The change in the temperature signal that would cause a transmission of one or more of the signals may comprise a change in temperature of 0.5 degrees Fahrenheit or Celsius (or the corresponding raw count value) or greater. Alternatively, a change in the temperature signal that could cause a transmission of one or more signals may comprise a first temperature measurement that is at least 0.5 degrees Fahrenheit or Celsius (or the corresponding raw count value) outside an acceptable temperature range for human skin. A change in humidity signal that would cause a transmission of one or more of the signals may comprise a first humidity signal that is less than 95% RH (or the corresponding raw count value). A change in skin proximity signal that would cause a transmission of one or more of the signals may comprise a change of at least 0.5 picoFarads above the background of a capacitive skin proximity sensor.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A waterless electrochemical transdermal alcohol sensor comprising:
    (a) a proton exchange membrane, wherein the proton exchange membrane is imbibed with an imbibing liquid, wherein the imbibing liquid comprises at least one cationic substance, the at least one cationic substance being liquid at room temperature;
    (b) a sensing electrode, wherein the sensing electrode is bonded to the proton exchange membrane;
    (c) a counter electrode, wherein the counter electrode is bonded to the proton exchange membrane; and
    (d) a reference electrode, wherein the reference electrode is bonded to the proton exchange membranes;
    (e) wherein the proton exchange membrane has two opposing surfaces, wherein the sensing electrode is bonded to one of the two opposing surfaces, and wherein both the counter electrode and the reference electrode are bonded to the other of the two opposing surfaces.

2. The waterless electrochemical transdermal alcohol sensor as claimed in claim 1 wherein the proton exchange membrane comprises a solid cation exchange membrane.

3. The waterless electrochemical transdermal alcohol sensor as claimed in claim 2 wherein the solid cation exchange membrane comprise a solid perfluorosulfonic acid membrane.

4. The waterless electrochemical transdermal alcohol sensor as claimed in claim 3 wherein the solid perfluorosulfonic acid membrane has an equivalent weight of approximately 700-1200 EW and has a thickness of approximately 0.003-0.015 inch.

5. The waterless electrochemical transdermal alcohol sensor as claimed in claim 1 wherein the at least one cationic substance comprises at least one member selected from the group consisting of a cationic liquid with an imidazolium backbone structure, a cationic liquid with a phosphonium backbone structure, a cationic liquid with an ammonium backbone structure, a cationic liquid with a pyridinium backbone structure, a cationic liquid with a pyrrolidinium backbone structure, and a cationic liquid with a sulfonium backbone structure.

6. The waterless electrochemical transdermal alcohol sensor as claimed in claim 5 wherein the cationic liquid with an imidazolium backbone structure is at least one member selected from the group consisting of 1-Ethyl-3-methylimidazolium tetrafluoroborate ($C_6H_{11}BF_4N_2$), 1-Butyl-3-methylimidazolium tetrafluoroborate ($C_8H_{15}BF_4N_2$), 1-Butyl-3-methylimidazolium hexafluoroantimonate ($C_8H_{15}F_6N_2Sb$), 1-Butyl-3-methylimidazolium hexafluorophosphate ($C_8H_{15}F_6N_2P$), 1-Dodecyl-3-methylimidazolium iodide ($C_{16}H_{31}IN_2$), 1-Ethyl-2,3-dimethylimidazolium trifluoromethane sulfonate ($C_8H_{13}F_3N_2O_3S$), 1-Ethyl-3-methylimidazolium thiocyanate ($C_7H_{11}N_3S$), 1-Ethyl-3-methylimidazolium trifluoromethane sulfonate ($C_7H_{11}F_3N_2O_3S$), 1-Butyl-3-methylimidazolium bis(trifluoromethyl sulfonyl) imide ($C_{10}H_{15}F_6N_3O_4S_2$), 1,2-Dimethyl-3-propylimidazolium bis(trifluoromethyl sulfonyl)imide ($C_{10}H_{15}F_6N_3O_4S_2$), 1,2-Dimethyl-3-propylimidazolium tris(trifluoromethyl sulfonyl)methide ($C_{12}H_{15}F_9N_2O_6S_3$), 1-Ethyl-3-methylimidazolium bis(pentafluoroethyl sulfonyl)imide ($C_{10}H_{11}N_3O_4S_2$), 1-Ethyl-3-methylimidazolium bis(trifluoromethyl sulfonyl)imide ($C_8H_{11}F_6N_3O_4S_2$), 1-Butyl-3-methylimidazolium methyl sulfate ($C_9H_{18}N_2O_4S$), 1-Ethyl-3-methylimidazolium ethyl sulfate ($C_8H_{16}N_2O_4S$) 1-Ethyl-3-methylimidazolium hydrogen sulfate ($C_6H_{12}N_2O_4S$), 1-Butyl-3-methylimidazolium thiocyanate ($C_9H_{15}N_3S$), and 1-Ethyl-3-methylimidazolium methanesulfonate ($C_7H_{14}N_2O_3S$).

7. The waterless electrochemical transdermal alcohol sensor as claimed in claim 5 wherein the cationic liquid with a phosphonium backbone structure is at least one member selected from the group consisting of Trihexyltetradecylphosphonium bis(2,4,4-trimethyl-8-pentyl)phosphinate ($C_{48}H_{102}O_2P_2$), Trihexyltetradecylphosphonium bis(trifluoromethylsulfonyl)amide ($C_{34}H_{68}F_6NO_4PS_2$), Trihexyltetradecylphosphonium decanoate ($C_{42}H_{87}O_2P$), Trihexyltetradecylphosphonium dicyanamide ($C_{34}H_{68}N_3P$), Trihexyltetradecylphosphonium hexafluorophosphate ($C_{32}H_{68}F_6P_2$), and Trihexyltetradecylphosphonium tetrafluoroborate ($C_{32}H_{68}BF_4P$), Triisobutylmethylphosphonium tosylate ($C_{20}H_{37}O_3PS$).

8. The waterless electrochemical transdermal alcohol sensor as claimed in claim 5 wherein the cationic liquid with an ammonium backbone structure is at least one member selected from the group consisting of Methyl-trioctylammonium bis(trifluoromethyl-sulfonyl)imide ($C_{27}H_{54}F_6N_2O_4S_2$), and tetrabutylammonium heptadecafluorooctanesulfonate ($C_{24}H_{36}F_{17}NO_3S$).

9. The waterless electrochemical transdermal alcohol sensor as claimed in claim 5 wherein the cationic liquid with a pyridinium backbone structure is at least one member selected from the group consisting of 1-Butyl-3-methylpyridinium bis(trifluoromethylsulfonyl)imide ($C_{12}H_{16}F_6N_2O_4S_2$), and 3-Methyl-1-propylpyridinium bis(trifluoromethylsulfonyl)-imide ($C_{11}H_{14}F_6N_2O_4S_2$).

10. The waterless electrochemical transdermal alcohol sensor as claimed in claim 5 wherein the cationic liquid with a pyrrolidinium backbone structure comprises 1-Butyl-1-methylpyrrolidinium bis(trifluoromethyl-sulfonyl)imide ($C_{11}H_{20}F_6N_2O_4S_2$).

11. The waterless electrochemical transdermal alcohol sensor as claimed in claim 5 wherein the cationic liquid with a sulfonium backbone structure comprises triethylsulfonium bis(trifluoromethylsulfonyl)imide ($C_8H_{15}F_6NO_4S_2$).

12. The waterless electrochemical transdermal alcohol sensor as claimed in claim 1 wherein the imbibing liquid consists of the at least one cationic substance.

13. The waterless electrochemical transdermal alcohol sensor as claimed in claim 1 wherein the imbibing liquid comprises the at least one cationic substance and a solvent, the at least one cationic substance being dissolved in the solvent.

14. The waterless electrochemical transdermal alcohol sensor as claimed in claim 13 wherein the solvent is selected from the group consisting of water, at least one alcohol, and combinations thereof.

15. The waterless electrochemical transdermal alcohol sensor as claimed in claim 13 wherein the concentration of the at least one cationic substance in the solvent comprises at least 30% cationic substance by volume.

16. The waterless electrochemical transdermal alcohol sensor as claimed in claim 1 wherein at least one of the sensing electrode, the counter electrode and the reference electrode comprises a substrate and a platinum-based catalyst, the platinum-based catalyst being coupled to the substrate.

17. The waterless electrochemical transdermal alcohol sensor as claimed in claim 16 wherein the substrate comprises a porous mesh or sinter fabricated from at least one material selected from the group consisting of platinum, gold, titanium, niobium, palladium, and gold.

18. The waterless electrochemical transdermal alcohol sensor as claimed in claim 16 wherein at least one of the sensing electrode, the counter electrode, and the reference electrode further comprises platinum particles, the platinum particles being interposed between the substrate and the platinum-based catalyst.

19. The waterless electrochemical transdermal alcohol sensor as claimed in claim 16 wherein the platinum-based catalyst comprises one of platinum-black, platinum on carbon, a bi-metallic alloy of platinum and a second metal on carbon, and a tri-metallic alloy of platinum and two other metals on carbon.

20. The waterless electrochemical transdermal alcohol sensor as claimed in claim 19 wherein the platinum-based catalyst comprises platinum on carbon and wherein the weight percentage of platinum in the platinum on carbon is approximately 10-70%, with the remainder being carbon.

21. The waterless electrochemical transdermal alcohol sensor as claimed in claim 19 wherein the platinum-based catalyst comprises the bi-metallic alloy of platinum and a second metal on carbon, wherein the second metal is selected from the group consisting of tin, ruthenium, palladium, nickel, cobalt, and tungsten, wherein the weight percentage of platinum in the bi-metallic alloy is approximately 20-70%, with the remainder being the second metal, and wherein the weight of the bi-metallic alloy is approximately 10-70%, with the remainder being carbon.

22. The waterless electrochemical transdermal alcohol sensor as claimed in claim 19 wherein the platinum-based catalyst comprises the tri-metallic alloy of platinum and two other metals on carbon, wherein the two other metals are two different metals selected from the group consisting of tin, ruthenium, palladium, nickel, cobalt, and tungsten, wherein the weight percentage of platinum in the tri-metallic alloy is approximately 10-70%, with the remainder being the two other metals in approximately a 1:1 ratio, by weight, with each other, and wherein the weight of the tri-metallic alloy is approximately 10-70%, with the remainder being carbon.

23. The waterless electrochemical transdermal alcohol sensor as claimed in claim 16 wherein the platinum-based catalyst further comprises an ionomer.

24. The waterless electrochemical transdermal alcohol sensor as claimed in claim 23 wherein the ionomer comprises perfluorosulfonic acid having an equivalent weight of approximately 700-1100 EW and wherein the ionomer is present in the platinum-based catalyst in an amount constituting about 10-60% by weight.

* * * * *